(12) United States Patent
Burling et al.

(10) Patent No.: US 8,231,922 B2
(45) Date of Patent: Jul. 31, 2012

(54) PHOSPHATIDYLSERINE ENRICHED MILK FRACTIONS FOR THE FORMULATION OF FUNCTIONAL FOODS

(75) Inventors: Hans Burling, Viby J (DK); Ingemar Andersson, Viby J (DK); Michael Schneider, Freinsheim (DE)

(73) Assignee: Arla Foods Amba, Viby (DK)

( * ) Notice: Subject to any disclaimer, the term of this patent is extended or adjusted under 35 U.S.C. 154(b) by 0 days.

(21) Appl. No.: 12/263,280

(22) Filed: Oct. 31, 2008

(65) Prior Publication Data

US 2009/0123630 A1    May 14, 2009

Related U.S. Application Data

(63) Continuation of application No. 11/442,975, filed on May 31, 2006, now abandoned.

(60) Provisional application No. 60/685,527, filed on May 31, 2005.

(51) Int. Cl.
*A23C 17/00* (2006.01)
(52) U.S. Cl. ......... 426/583; 424/439; 426/491; 426/580
(58) Field of Classification Search .................. None
See application file for complete search history.

(56) References Cited

U.S. PATENT DOCUMENTS

| | | | | |
|---|---|---|---|---|
| 4,447,463 A * | 5/1984 | Antenore et al. | ............. | 426/603 |
| 5,591,479 A | 1/1997 | Ponroy | | |
| 5,677,472 A | 10/1997 | Nyberg et al. | | |
| 6,531,148 B1 | 3/2003 | Enoki et al. | | |
| 7,189,418 B2 | 3/2007 | Hiratsuka et al. | | |
| 2004/0022922 A1 | 2/2004 | Rutenberg | | |
| 2004/0234587 A1 | 11/2004 | Sampalis | | |

FOREIGN PATENT DOCUMENTS

| | | |
|---|---|---|
| JP | 2003304814 | 10/2003 |
| JP | 2004 357699 | 12/2004 |
| WO | WO 2004/047566 | 6/2004 |
| WO | WO 2005/023271 A1 | 3/2005 |
| WO | WO 2005/027822 A2 | 3/2005 |
| WO | WO 2005/099876 A1 | 10/2005 |
| WO | WO 2006/041316 | 4/2006 |
| WO | WO 2006/041316 A1 | 4/2006 |

OTHER PUBLICATIONS

Miura et al., JAOCS, Jan. 2004, vol. 81, p. 97-100.*
Boyd et al., J Dairy Sci, 1999, vol. 82, p. 2550-2557.*
O'Connell et al., Journal of Dairy Science, 2000, vol. 83, No. 8, p. 1728-1732.*
Kidd P.M. (Functional Foods and Nutraceuticals, Dec. 2002, p. 1-11.*
Noh et al. (J Nutr, 2004, vol. 134, p. 2611-2616.*
Astaire et al., J. Dairy Sci, 2003, vol. 86, No. 7, p. 2297-2307.*
Hellhammer, J. et al., "Effects of Soy Lecithin Phosphatidic Acid and Phosphatidylserine Complex (PAS) on the Endocrine and Psychological Responses to Mental Stress," Stress (2004) 7(2):119-26.
Nutter, L.J. et al., "Determination of the Molecular Species Composition of Bovine Milk Serum Lecithin," J. Dairy Sci. (1967) 50(3):298-304.
Astaire et al., J. Dairy Sci. 2003, vol. 86, No. 7, p. 2297-2307.
Benton, D. et al., "The Influence of Phosphatidylserine Supplementation on Mood and Heart Rate When Faced With an Acute Stressor," Nutritional Neuroscience, vol. 4, pp. 169-178, 2001.
Blokland, Arjan et al., "Cognition-Enhancing Properties of Subchronic Phosphatidylserine (PS) Treatment in Middle-Aged Rats: Comparison of Bovine Cortex PS With Egg PS and Soybean PS," Nutrition, 1999, vol. 15, No. 10, pp. 778-783.
Database WPI—Section Ch, Week 200367, Derwent Publications Ltd., London, GB; Class D13, AN 2003-706261 XP002395571 & RU 2 210 925 C1 (Aug. 27, 2003).
Kirschbaum, Clemens et al., "The Trier Social Stress Test'—A Tool For Investigation Psychobiological Stress Responses in a Laboratory Setting," Neuropsychobiology, 1993, vol. 28, pp. 76-81.
Lambertsen & Christiansen, Scandinavian J. Nutrition, 1997, vol. 41, p. 88-90.
Vesper, Hubert et al., "Sphingolipids in Food and the Emerging Importance of Sphingolipids to Nutrition," J. Nutr., 1999, vol. 129, pp. 1239-1250.

* cited by examiner

*Primary Examiner* — Kade Ariani
(74) *Attorney, Agent, or Firm* — Finnegan Henderson Farabow Garrett & Dunner LLP

(57) ABSTRACT

Disclosed is a bovine milk derived phosphatidylserine source of natural composition having excellent dispersibility and organoleptic as well as physical stability. The source is useful in neutraceutical in powder, liquid or dispersion form. The source can be prepared from serum from butter oil production or from the retentate from microfiltration of whey for defatting purposes.

17 Claims, No Drawings

PHOSPHATIDYLSERINE ENRICHED MILK FRACTIONS FOR THE FORMULATION OF FUNCTIONAL FOODS

This is a continuation of application Ser. No. 11/442,975, filed May 31, 2006 now abandoned, and claims the benefit of U.S. Provisional Application No. 60/685,527, filed May 31, 2005, all of which are incorporated herein by reference.

The present invention is concerned with bovine phosphatidylserine, its preparation and use.

Phospholipids (PL) are very common substances in the biological world. They make up the membrane in most cells in both plants and animals. These lipids are organized in double layer structures serving as barriers between the various compartments and providing the proper environment for receptors, enzymes and transport proteins. They also serve as transmitters for communication between cells. A great part of the brain is made up by phospholipids. 15% of the human brain phospholipids pool consists of phosphatidylserine (PS). As brain ages, material is lost and replaced by inactive substances like cholesterol.

PS has lately been shown great interest as an active component in nutraceutical foods for improved cognitive performance, counteraction of memory loss and as a stress release agent. The literature is exemplified by article of Benton et al. Nutritional Neuroscience, Vol. 4 pp 169-178 with title "The influence of Phosphatidylserine Supplementation on Mood and Heart Rate when Faced with an Acute Stressor".

Trials have been performed over the years with significant positive results of intake of PS on stress and cognitive performance, see for example Arjan Blokland et al. "Cognition-Enhancing Properties of Subchronic Phosphatidylserine (PS) Treatment in Middle-Aged Rats: Comparison of Bovine Cortex PS With Egg PS and Soybean PS" in Nutrition Vol. 15, No. 10, 1999.

PS can be used as nutraceutical and introduced in various food formulations, drinks, tablets and different kind of bars containing a concentrate of health beneficial ingredients.

Historically, bovine brain was used as raw material for isolation of PS; but after the outbreak of mad cow disease (BSE) this material is not in use any more for obvious reasons.

During the last few years a semi-synthetic variant derived from soya lecithin has been developed and marketed by companies like Lucas Meyer GmbH/Degussa, Enzymotec, Chemi and Lipogen. We refer to WO 2005/027822. The principal procedure used by all mentioned manufacturers of PS is as far as we know making head group exchange of the phospholipids in the substrate, e.g. exchanging the choline group in phosphatidyl choline for serine using phospholipase D as active enzyme for the reaction to occur.

Because of the need to activate the enzyme with calcium in these procedures, PS often ends as a scarcely dispersible Ca salt. Purity of compound can vary from 20-90%. Another problem associated with the head group exchange procedure is small residues of phospholipase D enzyme activity, which leads to instability of PS in water-based liquid systems. An additional major problem with pure PL fractions derived as a whole is the development of very unpleasant taste in water-based systems. Because of these drawbacks, PS is marketed mostly in capsular form dissolved in oil. For the reasons given above, drink formulations of PS dispersed in water have not been successful so far.

Another problem in relation to marketing is the origin of PS. Head group exchanged PS is not of natural origin. It is in fact a semi-synthetic substance having all the restrictions imposed by the public health authorities for use in human food products.

In order to solve the problems described above, a new natural source of PS was searched for.

Milk contains phospholipids in the milk fat globule membrane (MFGM). This membrane is organized in ordered double layer structures together with special proteins, so-called MFGM proteins.

Special MFGM fragments originating from the golgi in the udder and from MFGM material ripped off the fat globules are present in skim milk.

After performing a solvent extraction procedure, the composition of the phospholipids can be determined, preferably by P 31 NMR (Spectral Service GmbH in Germany).

A typical composition of the PL pattern of milk is the following (P31 NMR method):

|  | Molar percentage |
| --- | --- |
| Phosphatidylcholine (PC) | 27 |
| Phosphatidylinositol (PI) | 7 |
| Phosphatidylserine (PS) | 13 |
| Sphingomyelin (SPH) | 25 |
| Phosphatidylethanolamine (PE) | 27 |
| Others | 1 |

The PL composition in milk is unique in nature due to the high contents of PS and sphingomyelin (SPH).

SPH is also a bioactive polar lipid in milk. It reduces the uptake of cholesterol, and is also regarded as having an anti-tumor effect in the colon. The active anticarcinogenic effect is traced to the degradation product of SPH in the intestinal tract, namely ceramide. We refer to Vesper et al. (1999) Sphingolipids in food and the emerging importance of sphingolipids to nutrition, J. Nutr. 129: p. 1239-1250.

Whole milk is a poor source of PS. It contains only about 27 mg of PS per litre. Skim milk contains about 10 mg/litre. Buttermilk from churning of cream contains about 130 mg of PS/litre. Buttermilk from butter oil is an even better source of PS, containing about 250 mg of PS/litre.

DEFINITIONS

The following terms used in the specification has the following meaning:

Nutraceutical is defined as any substance that is a food or part of a food and provides medical and/or health benefits, including the prevention and treatment of disease.

Buttermilk is defined as the serum phase after production of butter or butter oil PL is an abbreviation for phospholipids PS is an abbreviation for phosphatidylserine SPH is an abbreviation for sphingomyelin MFGM is an abbreviation for milk fat globule membrane PL concentrate as used in this invention is a phospholipid concentrate derived from bovine milk.

High performance liquid chromatography (HPLC) with P31 NMR detector is a advanced method for determining phospholipid composition including PS after solvent extraction of dried samples Trier Social Stress Test model (TSST) as described by Kirschbaum, C, Pirke, KM, Hellhammer, DH, The "Trier Social Stress Test" A tool for investigating psychobiological stress responses in a laboratory setting, Neurophysiobiology, 1993, 28, p. 76-81

Esprion 300 from DMV International is a whey protein concentrate with about 30% protein.

DESCRIPTION OF THE INVENTION

The present invention concerns a bovine milk derived phosphatidylserine source of natural composition having excellent dispersibility and organoleptic as well as physical stability.

Such a source can be derived from buttermilk or the serum phase from butter oil production. It can contain more than 0.2% PS calculated on the weight of the total solids, such as 0.2 to 10% PS or 1.5 to 3% PS calculated on the weight of the total solids.

A source of the invention can further supply sphingomyelin in an amount about twice the amount of phosphatidylserine.

Such a source is useful in a nutraceutical composition.

It can be a nutraceutical ingredient in form of a powder or liquid concentrate in dispersion or in solution.

Examples of nutraceutical compositions are chocolate, ice cream, drinks, yoghurt, nutritional bars or any nutraceutical formulation.

Especially it is possible to provide a nutraceutical composition in the form of a drink without problems of precipitation of active ingredient containing an amount of the source of the invention giving a drink containing more than 20 mg PS and more than 40 mg SPH per serving, such as 20 mg to 500 mg PS and 40 mg to 1500 mg SPH per serving.

The daily serving is usually 20 to 1000 ml or 100 to 250 ml.

The nutraceutical composition can also be formulated for intake in solid foods giving 20 mg to 500 mg PS and 40 mg to 1500 mg SPH per unit or dose.

All values between 20 mg and 500 mg PS and 40 and 1500 SPH can be used. There are no specific limits. However the effect of less than 20 mg PS and 40 mg SPH a day will be difficult to measure. More than 500 mg PS and 1500 mg SPH a day will not be harmful to health.

A nutraceutical composition can be based on milk or milk derived drinks like drinking yoghurt or ordinary yoghurt, any other type of drink, including water, acid fruit juice or similar fruit flavoured drinks having a pH in the range of 2 to 8.

The invention also relates to a process for the preparation of a bovine milk derived phosphotidylserine source from serum from production of butteroil comprising concentrating ordinary cream by centrifugation, whereafter the resulting emulsion is broken in a homogenizer, the serum phase is collected, fat-separated and treated by ultrafiltration including diafiltration and finally spray-dried.

Such a process can give a milk PL concentrate in which the phospholipid fraction comprises more than 75% of total lipids in the concentrate.

In such a process ordinary fat content of the cream is concentrated from about 40% to about 80%. The higher the fat concentration is in the cream before phase inversion the higher the PL content including phospahatidylserine in the serum phase.

The bovine milk derived phosphotidylserine source is also obtainable from the retentate from microfiltration of whey after defattening.

In order to obtain a powder containing high contents of primarily PS, cream for butteroil production is thus concentrated by centrifugation to a cream containing about 80% of fat. After breaking the emulsion by high shearing, a concentrated butter serum or buttermilk is obtained together with butteroil. The buttermilk so obtained is continuously fat-separated in the process, giving a serum containing about 70-80% of PL of total lipids in the serum. After this the serum is cooled and ultrafiltered to reduce the lactose and ash contents, and optionally by diafiltration to a retentate with about 17% PL of total lipids, and in particular about 2.0-2.5% of PS in total solids. This concentrate is finally spray-dried.

By following this procedure a good source of natural PS has been obtained with the following typical overall composition:

| | (%) | |
|---|---|---|
| Total lipids | 21-25 | |
| Phospholipids | 16-19 | (in particular about 2% of PS and 5% of sphingomyelin) |
| Protein | 55-60 | |
| Lactose | 6-9 | |
| Ash | 6 | |

Surprisingly, we found that when adding the material specified above to a drink base like water or skim milk, giving 100 mg of PS per 200 ml serving, we obtained a very efficient source of PS with no precipitation of PS and no deterioration of taste during long-term storage at refrigerator temperature.

EXAMPLES

Example 1

Effect of the Source of the Invention Compared with Soy PS Products Modified by Head-Group Exchange on the Market Three batches of 40 litres of skim milk stored in jacketed tanks were added with three different powders containing PS from different sources, namely:

Milk PL concentrate according to invention of buttermilk origin containing 2.0% of PS "PS 20" from Enzymotec in Israel containing 21% of PS. PS product from head group exchanged soya lecithin.

Ditto "PS 60" from Enzymotec, manufactured according to the same principle as "PS 20", containing 62% of PS.

PS addition was calculated to give a dose of 100 mg of PS for a 200 ml serving of the skim milk based drink.

The milk with added PS material was heated to 75° C. in a jacketed tank and held at the final temperature for 10 min.

The dispersion was homogenized in two steps, 40 and 160 bars, respectively, and UHT (ultra high temperature) treated at 142° C. for 6 s. After cooling, the product was packed in 500 ml sterile flasks and stored at 8° C. for three months.

The milk was tested for taste and PS content (P31 NMR) after one week; 1 month; two and three months.

The conclusion of the test was that the milk-added special fraction of buttermilk was physically and organoleptically stable.

The milk-added PS 20 and PS 60 were physically unstable. Already after one week, 70% of the PS had precipitated and settled at the bottom of the flasks. The drink made with PS from the source of the invention was found to be chemically stable throughout the test period and showed no precipitation.

As to organoleptic quality, the PS 20 sample had acquired an unpleasant off-taste typical for soya that made the milk almost undrinkable. The taste of the PS 60 sample was more stable during the test period.

In conclusion, according to the manufacturing procedure used, only the buttermilk derived PS according to the invention was long term physically stable giving no precipitation of active compound.

Example 2

240 metric tons of cream with 40% fat content was concentrated at 11.5 m$^3$/h at 70° C. in a centrifugal separator to give about 80% fat cream. The concentrated cream was in the next step phase inversed in a homogenizer and the serum phase, enriched in phospholipids, was removed at 1300 liter/h in a two-stage separation procedure and cooled to about 4° C. After ultrafiltration and drying of the serum phase (buttermilk) about 1.2 metric tons of milk PL concentrate was obtained with high proportion of PL in relation to is total lipids, i.e. 19% PL with a total lipids content of 23.3%. The composition of milk PL concentrate in more detail is described in the table below:

|  | (%) |
|---|---|
| Protein (Nx6.38, Kjeldahl) | 58.5 |
| Lactose | 6.6 |
| Ash | 5.3 |
| Moisture | 3.5 |
| Total lipids | 23.3 |
| Total phospholipids | 19.1 |
| Sphingomyelin | 5.1 |
| Phosphatidylcholine | 5.4 |
| Phosphatidylethanolamine | 4.3 |
| Phosphatidylserine | 2.3 |
| Phosphatidylinositol | 1.5 |
| Total ceramides | 1.3 |
| Gangliosides | 0.59 |
| Cholesterol | 0.27 |
| Triglycerides | appr. 3 |

Example 3

Formulation and Comparison and Clinical Trial

A test drink containing about 300 mg of phosphatidylserine per dose or serving of 250 ml was formulated using the milk PL concentrate produced in example 2. About 13.5 g milk PL powder was used to obtain the desired phosphatidylserine dose for a serving volume of 250 ml. The drink was used for clinical trial on Endocrine, Autonomic and Psychological parameters according to the Trier Social Stress Test model (TSST). The investigation was made at Institute Daacro/Diagnostic assessment and clinical research organization in Trier, Germany under the leadership of Dr Juliane Hellhammer.

A placebo drink was made on skim milk powder and butter oil. The drinks were homogenized at 50 bars and heat-treated at 143 deg. C. for 4 s.

The formulations were flavoured by a vanilla extract and sweetened by addition of sucralose. The lactose was adjusted in the test drink to contain the same content as the placebo. The placebo drink contained almost no phospholipids, which was ascertained after analysis. Both test and placebo contained were thus equivalent in relation to lipids (1.3%), protein (3.2%) and lactose (4.4%).

Both test sample and placebo were perfectly stable on storage for at least 4 months and created no off-tastes.

The clinical trial comprised in total 46 patients in a double blind arrangement. The test and placebo drinks were consumed in a controlled way for three weeks, where after the patients were exposed to the stress test TSST/Trier Social Stress Test. Both physiological, endocrine and cognitive parameters as memory, mood/stress were measured and compared between the groups.

Result of Clinical Test:

The following summary was given from the evaluation of trial:

Taken together the results of the present study suggest that intake of 13.5 g milk PL powder as specified above (i.e. an additive of the invention) in a drink formulation give strong indications of enhancing working memory performance while dampening the physiological and endocrine stress responses. The contents of serum and saliva cortisol levels were e.g. significantly lowered in the test group.

In addition it was noted that the cholesterol (LDL) was significantly reduced by about 10% in the blood serum of the test group in comparison with the placebo group. The HDL value was not influenced.

Example 4

Milk Chocolate Formulation

Milk chocolate added milk PL concentrate was manufactured according to the following recipe giving a batch of 100 kg finished product.

|  | Quantity (kg) |
|---|---|
| Sugar | 39.00 |
| Cocoa mass | 16.50 |
| Cocoa butter | 18.50 |
| Lactose | 4.00 |
| Milk powder | 17.50 |
| Milk PL powder | 4.50 |
| Vanillin | 0.03 |

The product was physically and organoleptically fully comparable with reference without milk PL. A daily portion of 100 g of chocolate would provide 100 mg of PS (plus 160 mg SPH)

Example 5

Ice Cream Formulation

Ice cream was made according to the following recipe giving a batch of 100 kg.

|  | Quantity (kg) |
|---|---|
| Cream (40% fat) | 25.00 |
| SMP (Skim milk powder) | 3.62 |
| Esprion 300 (whey protein concentrate) | 0.67 |
| Sugar | 9.00 |
| Fructose syrup | 9.00 |
| Emulsifier (LBG) | 0.12 |
| Guar gum | 0.08 |
| Milk PL powder | 4.33 |
| Water | to 100 |

A normal daily portion of ice cream is 75 g. At 4.33% milk PL powder with 2.2% PS the daily amount of PS is 70 mg (160 mg SPH). The product was comparable to reference both according to taste and stability. The amount of emulsifier could be reduced significantly in the test product.

The invention claimed is:

1. A source of bovine milk derived phosphatidylserine wherein said source contains 0.2 to 10% phosphatidylserine calculated based on the weight of total solids, and wherein said source has a phopholipid content of 16-19% and a protein content of 55-60%.

2. The source of claim 1 containing 1.5 to 3% phosphatidylserine calculated on the weight of total solids.

3. The source of claim 1 supplying sphingomyelin in an amount about twice the amount of phosphatidylserine.

4. A nutraceutical composition which contains the source of bovine milk derived phosphatidylserine as recited in claim 1.

5. The nutraceutical composition of claim 4 in the form of a chocolate, an ice cream, a drink, a yoghurt, or a nutritional bar.

6. The nutraceutical composition of claim 5 in the form of a drink containing more than 20 mg phosphatidylserine and more than 40 mg sphingomyelin per serving.

7. The nutraceutical composition of claim 6 in the form of a drink containing 20 mg to 500 mg phosphatidylserine and 40 mg to 1500 mg sphingomyelin per serving.

8. The nutraceutical composition of claim 7 where the daily serving is 20 to 1000 ml.

9. The nutraceutical composition of claim 8 where the daily serving is 100 to 250 ml.

10. The nutraceutical composition of claim 5 wherein the composition contains 20 mg to 500 mg phosphatidylserine and 40 mg to 1500 mg sphingomyelin per unit or dose.

11. The nutraceutical composition of claim 4 based on milk.

12. The nutraceutical composition of claim 4 wherein the composition is a water-based drink, an acid fruit juice or a fruit flavoured drink having a pH in the range of 2 to 8.

13. The source of bovine milk derived phosphatidylserine according to claim 1 comprising the steps of centrifuging cream to a cream containing about 80% of fat, breaking the resulting emulsion by high shearing, to obtain a butter milk together with butteroil, collecting the butter milk, separating the fat from the butter milk, treating the fat-separated butter milk by ultrafiltration and spray-drying the resulting phosphatidylserine source.

14. The phosphatidylserine source according to claim 13 in which the phospholipid fraction comprises more than 75% of total lipids in the resulting phosphatidylserine source.

15. The phosphatidylserine source of claim 13 where the fat content of the cream is concentrated from about 40% to about 80%.

16. The phosphatidylserine source of claim 13, wherein ultrafiltration includes diafiltration.

17. The phosphatidylserine source of claim 1, wherein the source contains sphingomyelin in an amount about twice the amount of phosphatidylserine.

* * * * *